United States Patent [19]
Grandjean

[11] Patent Number: 5,716,391
[45] Date of Patent: Feb. 10, 1998

[54] MEDICAL ELECTRICAL LEAD HAVING TEMPORARILY RIGID FIXATION

[75] Inventor: Pierre Andre Grandjean, Warsage, Belgium

[73] Assignee: Medtronic, Inc., Minneapolis, Minn.

[21] Appl. No.: 526,055

[22] Filed: Aug. 23, 1995

[51] Int. Cl.[6] ............................................. A61N 1/05
[52] U.S. Cl. ................................... 607/127; 607/126
[58] Field of Search ................................ 607/126, 127, 607/128, 129, 130, 131, 119, 122

[56] References Cited

U.S. PATENT DOCUMENTS

| | | | |
|---|---|---|---|
| 4,000,745 | 1/1977 | Goldberg | 607/127 |
| 4,010,758 | 3/1977 | Rockland et al. | 607/131 |
| 4,258,724 | 3/1981 | Balat et al. | 607/128 |
| 4,628,944 | 12/1986 | MacGregor et al. | 607/126 |
| 4,827,940 | 5/1989 | Mayer et al. | 607/131 |
| 4,876,109 | 10/1989 | Mayer et al. | 427/224 |
| 4,913,147 | 4/1990 | Fahlstrom et al. | 607/2 |
| 4,936,835 | 6/1990 | Haaga | 604/265 |
| 5,003,990 | 4/1991 | Osypka | 607/127 |
| 5,049,138 | 9/1991 | Chevalier et al. | 604/265 |
| 5,080,655 | 1/1992 | Haaga | 604/265 |
| 5,085,218 | 2/1992 | Heil, Jr. et al. | 607/140 |
| 5,129,404 | 7/1992 | Spehr et al. | 607/127 |
| 5,143,090 | 9/1992 | Dutcher et al. | 607/131 |
| 5,374,287 | 12/1994 | Rubin | 607/131 |
| 5,522,876 | 6/1996 | Rusink | 607/122 |
| 5,531,783 | 7/1996 | Giele et al. | 607/126 |

FOREIGN PATENT DOCUMENTS 1277107  6/1972  United Kingdom ............ A61N 1/04

*Primary Examiner*—Marvin M. Lateef
*Assistant Examiner*—Carl H. Layno
*Attorney, Agent, or Firm*—Michael J. Jaro; Harold Patton

[57] ABSTRACT

A medical electrical lead having active fixation which readily flexes within the cardiac tissue through a fixation mechanism which is temporarily rigid. In a preferred embodiment, the medical electrical lead features a fixation helix constructed from an absorbable material, such as mannitol. In an alternate embodiment a medical electrical lead is disclosed which features a fixation mechanism having a multi-layer construction. In that embodiment the fixation mechanism is fashioned of a first, rigid and absorbable, material and a second, readily pliable and nonabsorbable, material. Through such a construction the lead may be fixed in the tissue such that over time the first material is absorbed by the body and the second material is left in position to flexibly fix the lead in place. In one embodiment the second material is conductive and is used to achieve an electrical coupling to the body tissue.

10 Claims, 5 Drawing Sheets

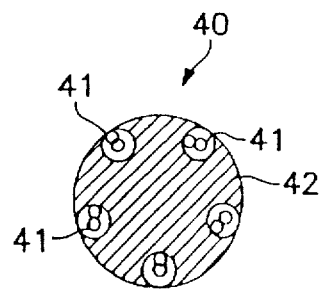
FIG. 5
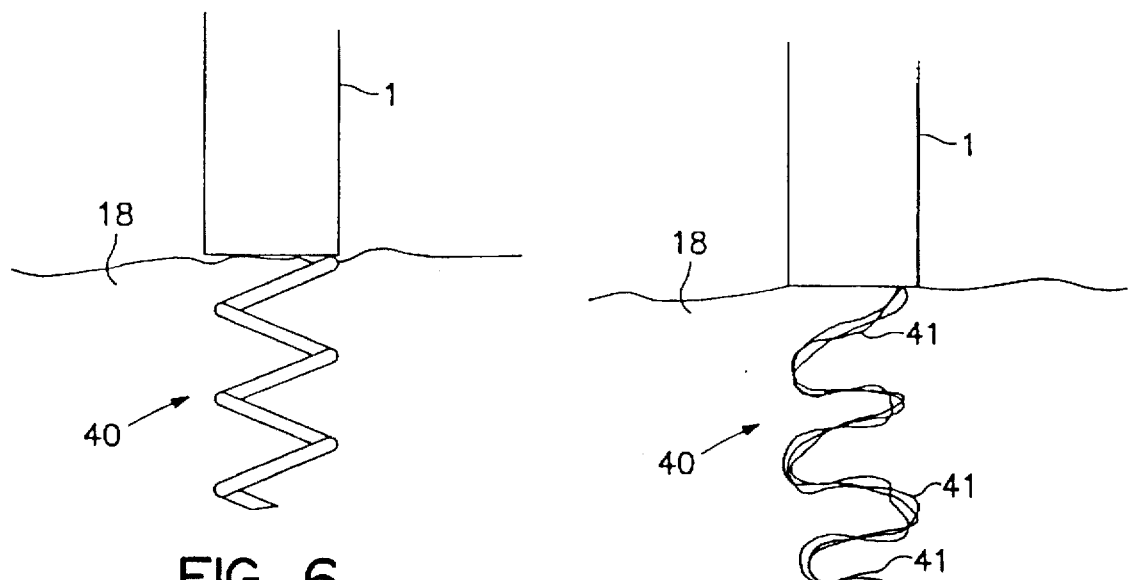
FIG. 6
FIG. 7

MEDICAL ELECTRICAL LEAD HAVING TEMPORARILY RIGID FIXATION

FIELD OF THE INVENTION

This invention relates generally to the field of implantable medical devices, and more particularly to a medical electrical lead which features a fixation mechanism which is temporarily rigid.

BACKGROUND OF THE INVENTION

In the medical field, various types of implantable leads are known and used. Cardiac pulse generators, in particular, use implantable leads to both sense cardiac function and deliver stimulation pulses. One type of commonly used implantable lead is an endocardial lead.

Endocardial leads are attached at their proximal end to an implantable pulse generator and at their distal end to the endocardium of a cardiac chamber. Often the lead assembly is inserted into the heart through a vein. The lead generally has an inner conductor covered by an insulative sheath.

The distal end of an endocardial lead may electrically couple with the endocardium by either an active fixation mechanism or a passive fixation mechanism. Passive fixation mechanisms, such as a tine assembly, lodge or passively fix the lead to the heart. Active fixation mechanisms use a structure, such as a helix or hook, to engage into or actively fix themselves to the heart.

A sharpened helix has been found to provide a reasonably secure means for fixing the lead to the heart. One drawback to the use of a helix is the tissue reaction between the ever-moving heart tissue and the rigid helix. Specifically, because the heart is a constantly moving organ, the presence of a stationary and stiff fixation coil exacerbates the normal build-up of collagen and fat near the implanted helical coil. Such tissues may detrimentally affect the electrical performance of the surrounding tissue. As a result, if the helix itself is used as the electrode, or even if the electrode is near the helix, the stimulation thresholds may rise.

In particular, maintaining stimulation thresholds is important. Implantable pulse generators are battery-powered and thus have a finite operating life. Over time, the battery will be depleted; ultimately the implanted pulse generator must be replaced. Replacement involves a surgical procedure. Therefore, it is important to minimize the electrical current drain on the battery. A lead which minimizes such drain by maintaining stimulation thresholds is desired. One approach to maintain the thresholds is to prevent the build-up of tissues such as collagen and fat around the fixation mechanism.

SUMMARY OF THE INVENTION

The present invention is directed to a medical electrical lead having active fixation which readily flexes within the cardiac tissue. In particular the present invention is a medical electrical lead having fixation mechanism which is temporarily rigid. In a preferred embodiment of the invention, the medical electrical lead features a fixation helix constructed from an absorbable material, such as mannitol. In an alternate embodiment of the present invention, a medical electrical lead is disclosed which features a fixation mechanism having a multi-layer construction. In that embodiment the fixation mechanism is fashioned of a first, rigid and absorbable, material and a second, readily pliable and nonabsorbable, material. Through such a construction the lead may be fixed in the tissue such that over time the first material is absorbed by the body and the second material is left in position to flexibly fix the lead in place. In one embodiment the second material is conductive and is used to achieve an electrical coupling to the body tissue.

BRIEF DESCRIPTION OF THE DRAWINGS

FIG. 5 is a cross-sectional view of an alternate embodiment fixation mechanism.

FIG. 6 depict an alternate embodiment fixation mechanism immediately after being implanted within body tissue and having the temporarily rigid and absorbable material not yet absorbed.

FIG. 7 depict the alternate embodiment fixation mechanism shown in FIG. 6 after implanted within body tissue and having the absorbable material absorbed.

The drawings are not necessarily to scale.

DETAILED DESCRIPTION OF THE PRESENT INVENTION

The present invention is not limited to only fix atrial or ventricular pacing leads, and may be employed in fixing many of various types of therapeutic or diagnostic devices including nerve, muscle or defibrillation leads. It is to be further understood, moreover, the present invention may be employed in many of various types of therapeutic or diagnostic catheters and is not limited only to the fixing of electrical leads. For purposes of illustration only, however, the present invention is below described in the context of endocardial pacing leads.

Figure 1:
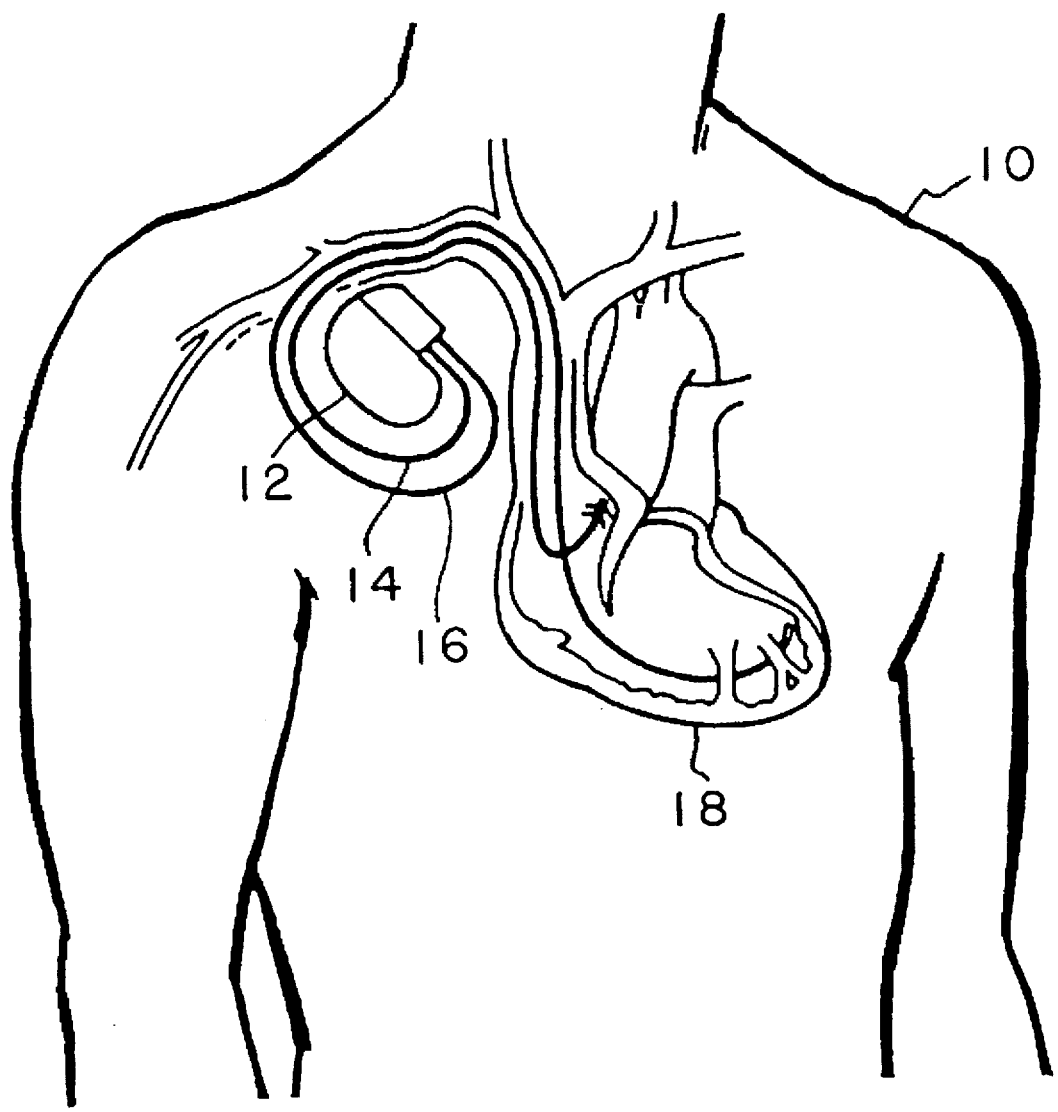
FIG. 1 depicts the venous positioning and placement of transvenous endocardial leads in a patient.

FIG. 1 depicts a typical arrangement of a pacing system implanted in a patient 10, the pacing system comprising a subcutaneously disposed pacemaker 12 and transvenous endocardial pacing leads 14 and 16. In FIG. 1, the distal end of pacing lead 14 is shown disposed generally in the atrial region of the patient's heart 18, while the distal end of pacing lead 16 is disposed generally in the ventricular region of heart 18.

Figure 2:
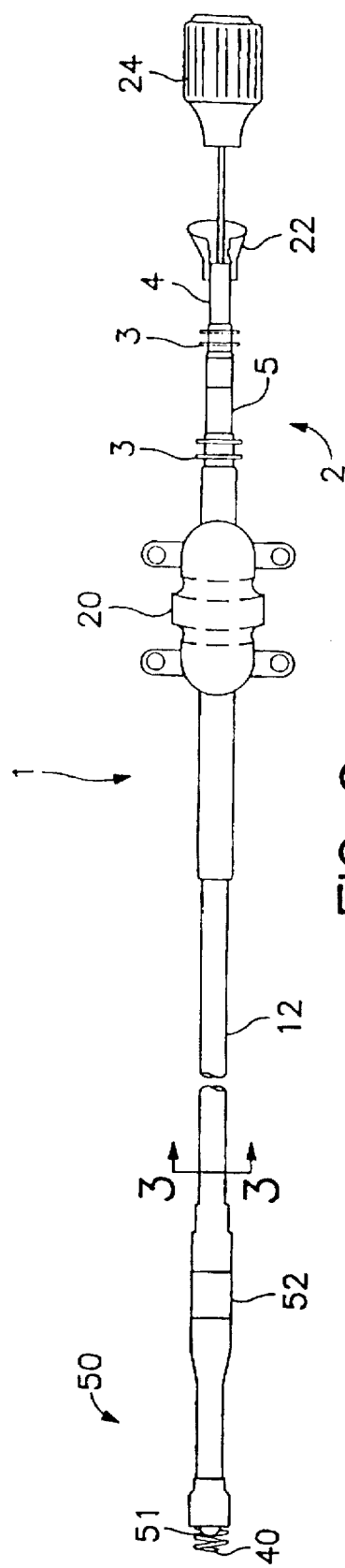
FIG. 2 depicts a body-implantable, endocardial fixed screw lead according to the present invention.

FIG. 2 depicts in general the configuration of lead 1. As seen lead 1 has connector assembly 2 at proximal end for coupling lead 1 to an implantable pulse generator (not shown in this Figure.) Connector assembly 2 preferably has sealing rings 3, terminal pin 4 and terminal ring 5 all of a type known in the art. Of course, other types of connector assemblies may be used, such as simple pins or even stripped or exposed wire.

An anchoring sleeve 20 (shown partially in cross-section) may also be provided for suturing lead 1 to body tissue.

Anchoring sleeve 20 and connector assembly 2 are preferably fabricated from silicone rubber, although they may also be constructed of any other suitable biocompatible material known in the art.

Lead 1 may also include stylet guide 22 (shown in partial cut-away) and stylet assembly 24 coupled to connector assembly 2 for imparting stiffness to lead 1 during placement and for actuation of the lead's fixation mechanism 40, described below. Stylet guide 22 and stylet assembly 24 are typically discarded after use and before connection of terminal pin 4 to a pulse generator.

Electrode 50 and fixation assembly 40 are disposed at distal end of lead 1. Electrode is bipolar consisting of tip electrode 51 and ring electrode 52. As will be appreciated by those of ordinary skill in the art, tip electrode 51 and ring electrode 52 are coupled to separate, insulated lead conductors (not shown in FIG. 2 but seen in FIG. 3) which extend along the length of lead body 12.

Tip electrode 51 used in the lead shown in FIG. 2 is preferably fashioned using a porous platinum composition coated with platinum black. The porosity, together with the platinum black coating is intended to reduce source impedance and polarization. Although platinum is the preferred other materials may also be used, including but not limited to such materials as palladium, titanium, tantalum, rhodium, iridium, carbon, vitreous carbon and alloys, oxides and nitrides of such metals or other conductive materials. Of course, some materials are incompatible with others and may not be effectively used together. The limitations of specific materials for use with others is well known in the art. Examples of acceptable electrode materials and associated fabrication techniques employed to achieve the microporous structure may be found in Stokes, U.S. Pat. No. 4,506,680 and related Medtronic U.S. Pat. Nos. 4,577,642; 4,606,118 and 4,711,251 and in the Richter et al., U.S. Pat. No. 4,773,433; Heil Jr. et al., U.S. Pat. No. 4,819,661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603,704; Skalsky et al., U.S. Pat. No. 4,784,161; Szilagyi, U.S. Pat. No. 4,784,160, each of which is herein incorporated by reference.

Although not shown in FIG. 2, lead 1 preferably includes a monolithic controlled release device (MCRD) preferably constructed from silicone rubber to elute an anti-inflammatory agent proximate electrode 51. The anti-inflammatory agent, preferably a derivative of dexamethasone, such as the steroid dexamethasone sodium phosphate, is loaded in MCRD. The steroid also is deposited within electrode 51 material by application of a solution of dexamethasone sodium phosphate dissolved in a mixture of isopropanol and distilled or deionized water.

Figure 3:
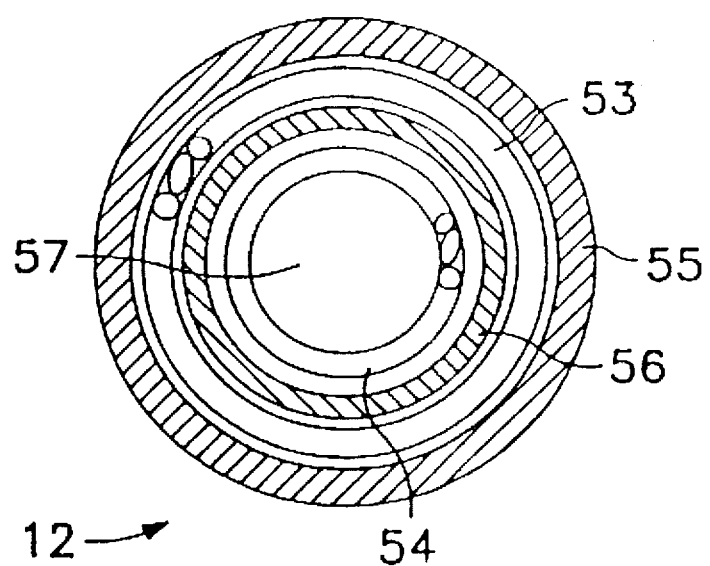
FIG. 3 shows a view of the lead of FIG. 2 along the line 3—3.

Turning now to FIG. 3, lead body 12 has concentric multi-filar conductor coils 53, 54 of a platinum-iridium alloy or any other suitable alloy, such as MP35N located between concentric insulative sheaths 55, 56 made of silicone rubber, polyureathane, or the like. This configuration allows for coils 53, 54 to be insulated throughout their respective lengths. Coil 53 is electrically coupled with ring electrode 52, while coil 54 is electrically coupled with tip electrode 51. Lumen 57 exists along the length of lead body 12, such that a stylet may be received therein.

Fixation mechanism 40 is preferably constructed of an absorbable material. In the preferred embodiment this material is mannitol which is tailored to absorb within one day after implantation. This amount of time corresponds to the amount of time after implantation a thrombic capsule begins to envelop lead 1, or at least a portion thereof, and maintain the position of lead 1. Thrombic capsule, in time, transforms to a fibrotic capsule. In such a manner lead 1 is chronically fixed in position. Thus the rigid fixation mechanism 40 only mechanically fixes lead 1 in the tissue for a limited time. Because fixation mechanism 40 is only temporarily rigid within the tissue, the reaction between the rigid helix and the ever-moving heart tissue is minimized, i.e. the build-up of collagen and fat near the helical coil is minimized. Thus the electrical performance of the surrounding tissue is maintained over time.

Although in the preferred embodiment mannitol is used for fixation mechanism 40, other materials may also be used.

Figure 4:
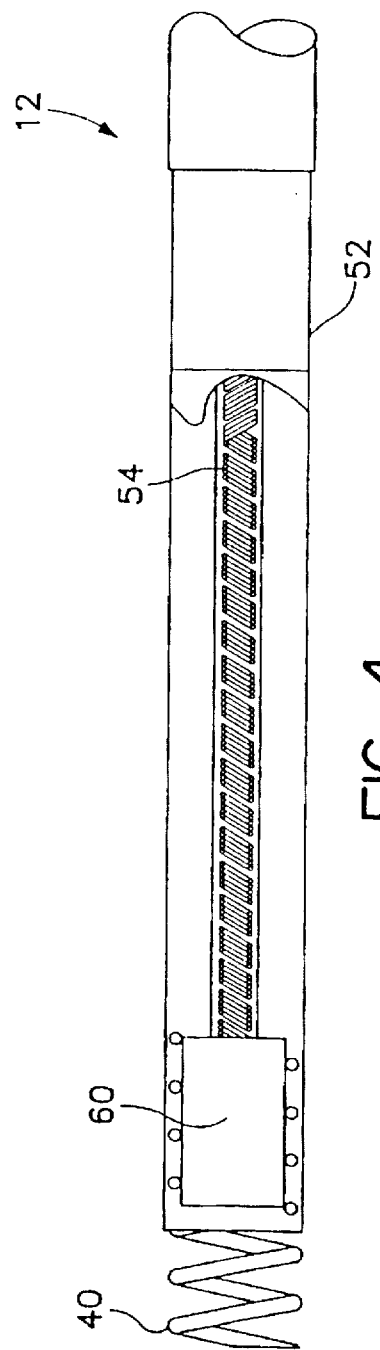
FIG. 4 depicts an alternate embodiment of a body-implantable, endocardial fixed screw lead according to the present invention.

In an alternate embodiment fixation mechanism 40 may be also used as an electrode. Such a configuration is seen in FIG. 4, which is a sectional view of a distal end of a lead. Ring electrode 52 is coupled to outer conductor 53 (not seen in this view.) Inner conductor 54 runs to the distal end of lead 1 and is coupled to crimp core 60. Crimp core 60, in turn, is coupled to fixation mechanism 40. In this embodiment fixation mechanism 40 is a composite of a first conductive and readily pliable material and a second rigid and absorbable material.

A cross-sectional view of composite fixation mechanism 40 may be seen in FIG. 5. As seen composite fixation mechanism 40 is fashioned from one or more element 41 and absorbable material 42. Element 41 and absorbable material 42 are integral with one another such that fixation mechanism 40 is a one piece unit. Element 41 is preferably a coiled conductor and fashioned from MP35N, although other types of conductors may also be used, such as bundled stranded wire. In addition, if element 41 is not used for to electrically couple to body tissue, then element 41 may also be any other acceptable biocompatible material, such as polyester strands. Absorbable material 42 is preferably mannitol. Element 41 is molded within absorbable material 42, as seen in FIG. 5. The overall composite fixation mechanism 40 is fashioned in a helical shape, as seen in FIG. 4. Through such a construction the lead may be fixed in the tissue such that over time the second material is absorbed by the body and the first material is left in position to flexibly fix the lead in place.

Essentially absorbable material 42 is relatively rigid, while element 41 is readily flexible. As seen in a comparison of FIGS. 6 and 7, fixation mechanism 40 is introduced in the tissue and, over time, rigid absorbable material 42 is absorbed and only readily flexible element 41 remains in the tissue. In the preferred embodiment element 41 is a coiled conductor. Thus in the preferred embodiment the remaining structure within the tissue is a relatively flexible conductor. Through such a structure then an electrical interface with the tissue may be achieved without causing a decrease in electrical characteristics of the tissue due to the replacement of tissue over time with collagen or fat or both. It should be noted that this electrical coupling of lead 1 to tissue 18 may be achieved through either the conductive element 41 as depicted in FIG. 7 as well as through a tip electrode 51, as seen in the embodiment of FIG. 2.

Figure 8:
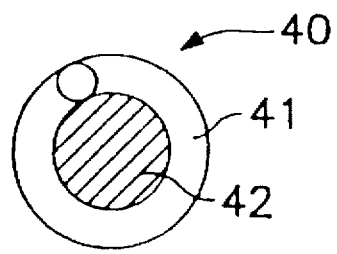
FIG. 8 is a cross-sectional view of an alternate embodiment fixation mechanism.

FIG. 8 is a cross-sectional view of a further alternate embodiment fixation mechanism. As seen composite fixation mechanism 40 is fashioned from element 41 with a rigid central core of absorbable material 42. Absorbable material 42 is preferably mannitol. Element 41 is preferably a coiled conductor and fashioned from MP35N. It is also possible to use a nonconductive material such as a nylon cord in place of the coiled conductor of element 41. Of course, if such other materials are used other than a conductor, then the fixation mechanism 40 may not be available to use as an electrode.

Figures 9, 10:
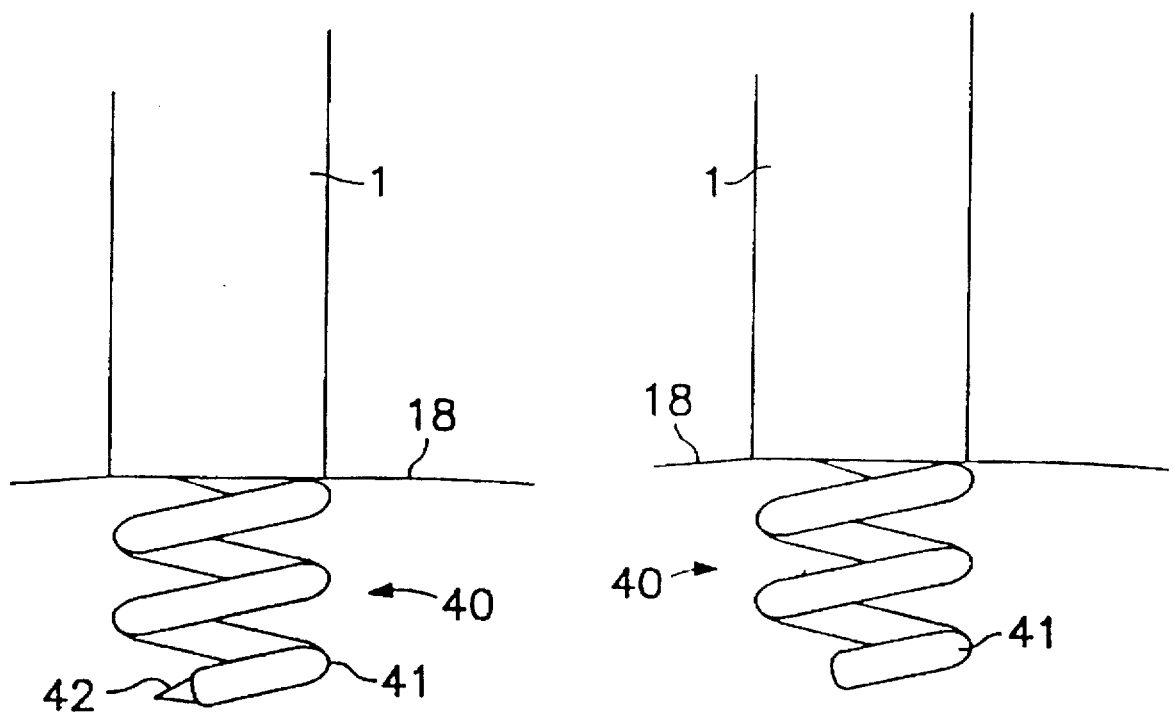
FIG. 9 depicts an alternate embodiment fixation mechanism implanted immediately after being implanted within body tissue and having the temporarily rigid and absorbable material not yet absorbed.
FIG. 10 depict the alternate embodiment fixation mechanism shown in FIG. 9 after implanted within body tissue and having the absorbable material absorbed.

The overall composite fixation mechanism 40 is fashioned in a helical shape, as seen in FIGS. 9 and 10. It should be noted the in this embodiment absorbable material 42 is fashioned to extend beyond the end of element 41 so as to have a pointed tip, as best seen in FIG. 9. As seen, element 41 comprises a coiled conductor. The coiled conductor, in turn, is wound into a helical shape, with absorbable material 42 at the center. Through such a construction lead 1 may be fixed in the tissue by screwing fixation mechanism 40 into cardiac tissue 18. As seen in a comparisons of FIGS. 9 and 10, once implanted rigid absorbable material 42 of fixation mechanism 40 is absorbed and only readily flexible element 41 remains in the tissue. Thus in this embodiment the remaining structure within the tissue is a relatively flexible conductor.

While the invention has been described in the context of the fixing of endocardial pacing leads, the present invention is not limited to only endocardial leads, but may also be used within a myocardial or epicardial lead. Indeed, the present invention is not limited to only fix cardiac pacing leads, and may be employed in fixing many of various types of therapeutic or diagnostic devices including nerve, muscle or defibrillation leads. It is to be further understood, moreover, the present invention may be employed in many of various types of therapeutic or diagnostic catheters and is not limited only to the fixing of only electrical leads.

Finally, although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A medical electrical lead comprising:

a lead body, the lead body having a first conductor;

an inner insulative sleeve positioned over the first conductor;

a connector assembly positioned on a proximal end of the lead body and coupled to the first conductor, and an electrode assembly disposed at the distal end of the lead body and coupled to the first conductor; and a fixation mechanism disposed at the distal end of the lead body, the fixation mechanism constructed of a first material and a second material, wherein the first material has means for inserting the first material into body tissue, the first material further being absorbable into body tissue, wherein said first material and said second material comprise an integral piece and wherein the first material has a helical shape.

2. A lead in accordance with claim 1 wherein first material uniformly covers the second material.

3. A lead in accordance with claim 1 wherein the first conductor comprises a coiled conductor.

4. A lead in accordance with claim 1 wherein the second material comprises a conductor.

5. A lead in accordance with claim 1 wherein the second material comprises a coiled conductor.

6. A lead in accordance with claim 1 wherein the second material comprises a bundled stranded wire.

7. A lead in accordance with claim 1 wherein the first material comprises mannitol.

8. A medical electrical lead comprising:

a lead body, the lead body having a first conductor;

an inner insulative sleeve positioned over the first conductor;

a connector assembly positioned on a proximal end of the lead body and coupled to the first conductor;

an electrode assembly disposed at the distal end of the lead body and coupled to the first conductor; and a fixation mechanism disposed at the distal end of the lead body, the fixation mechanism comprising a first member, the first member having a first stiffness, a second member, the second member having a second stiffness, the second stiffness less than the first stiffness, the second member being absorbable by body tissue, wherein said first material and said second material comprise an integral piece and wherein the first and second members have helical shapes.

9. A lead in accordance with claim 8 wherein the first material comprises a conductor.

10. A fixation device for a body-implantable device comprising:

a connector assembly;

a conductor connected to the connector assembly;

an electrode connected to the conductor;

an insulative sheath covering the conductor between the connector assembly and the electrode; and means for fixing, the means for fixing connected to the insulative sheath, the means for fixing being absorbable wherein the means for fixing comprise a first member, the first member being conductive and flexible, and a second member, the second member being stiff and absorbable, the second member integral with the first member, the second member being helical.

* * * * *